United States Patent [19]

Lucas et al.

[11] Patent Number: 5,643,852

[45] Date of Patent: Jul. 1, 1997

[54] FUNGICIDAL COMPOSITIONS FOR THE ENHANCEMENT OF TURF QUALITY

[75] Inventors: Leon T. Lucas, Raleigh, N.C.; Laurence C. Mudge, Camden, S.C.

[73] Assignee: North Carolina State University, Raleigh, N.C.

[21] Appl. No.: 415,635

[22] Filed: Apr. 3, 1995

Related U.S. Application Data

[63] Continuation-in-part of Ser. No. 3,632, May 12, 1994, Pat. No. 5,336,661.

[51] Int. Cl.$^6$ .......................... A01N 47/14; A01N 57/12; A01N 59/06
[52] U.S. Cl. .......................... 504/126; 504/143; 504/129; 504/116; 514/141; 514/491
[58] Field of Search .......................... 504/126, 143, 504/116; 514/141, 491

[56] References Cited

U.S. PATENT DOCUMENTS

| | | | |
|---|---|---|---|
| 2,129,013 | 9/1938 | Linstead et al. | 260/314 |
| 2,214,454 | 9/1940 | Dent | 260/314 |
| 2,276,860 | 3/1942 | Niemann et al. | 260/314 |
| 2,452,606 | 11/1948 | Roselle | 106/289 |
| 2,460,779 | 2/1949 | Brouillard et al. | 260/314.5 |
| 2,460,783 | 2/1949 | Lecher et al. | 260/314.5 |
| 2,471,794 | 5/1949 | Sumner | 260/314.5 |
| 2,485,167 | 10/1949 | Rintelman | 260/314.5 |
| 2,485,168 | 10/1949 | Rintelman | 260/314.5 |
| 2,556,729 | 6/1951 | Bridgeton | 260/314.5 |
| 2,613,128 | 10/1952 | Baumann et al. | 8/28 |
| 3,379,610 | 4/1968 | Lyon et al. | 167/22 |
| 3,632,328 | 1/1972 | Gaskin et al. | 71/3 |
| 3,935,242 | 1/1976 | Fulconis et al. | 260/429 |
| 3,950,265 | 4/1976 | Albrecht et al. | 252/311 |
| 4,394,316 | 7/1983 | Chao | 260/429 |
| 4,806,445 | 2/1989 | Horriere et al. | 514/141 |
| 4,956,183 | 9/1990 | Miki et al. | 424/630 |
| 5,171,853 | 12/1992 | Thorp et al. | 536/27 |
| 5,336,661 | 8/1994 | Lucas | 504/126 |
| 5,350,843 | 9/1994 | Itoh et al. | 540/138 |
| 5,380,842 | 1/1995 | Itoh et al. | 540/128 |

FOREIGN PATENT DOCUMENTS

| | | |
|---|---|---|
| 1-562-940 | 3/1969 | France. |
| 25 11 077 | 3/1975 | Germany. |
| 2412324 | 9/1975 | Germany. |
| 2511077 | 9/1976 | Germany. |
| 82034781 | 7/1982 | Japan. |
| 1-157904 | 6/1989 | Japan. |
| 6-73397 | 3/1994 | Japan. |

OTHER PUBLICATIONS

FORE, Speciment Label, Apr. 1985.
CHIPCO, Speciment Label, 1992.
S. Lessage, Reduction of the Formation of Ethylenethiourea from Ethylenebis (dithiocarbamates) by Cupric Ions in Aqueous Media, *J. Agric. Food Chem.* 28(4), pp. 787–790 (1980).
A. Stevenson, Fungicidal Compositions, *Patent Journal,* p. 39 (Jul. 26, 1967).
N. M. Bigelow et al., Phthalocyanine Pigments, *The Chemistry of Synthetic Dyes and Pigments,* pp. 577–606. (1972).
W. S. Struve, Phthalocyanine Dyes, *The Chemistry of Synthetic Dyes and Pigments,* pp. 607–624 (1972).
T. Ostmeyer, The Color Green, *Golf Course Management* pp. 40–44 (Aug. 1994).
M.E. Fenn et al; Studies on the In Vitro and In Vivo Antifungal Activity of Fosetyl–Al and Phosphorous Acid, *Phytopathology* 74 No. 5, pp. 606–611 (1984).

*Primary Examiner*—Richard L. Raymond
*Assistant Examiner*—Brian G. Bembenick
*Attorney, Agent, or Firm*—Bell, Seltzer, Park & Gibson

[57] ABSTRACT

Fungicidal compositions for the protection of turfgrass against crown and root rot are disclosed. The compositions comprise, as the active material, (a) a monoester salt of a phosphorous acid (preferably aluminum ethyl phosphite), (b) an ethylene bisdithiocarbamate contact fungicide (preferably manganese-zinc ethylene bisdithiocarbamate), and (c) a benzoporphyrin compound. Preferred compositions comprise 1 part by weight of the monoester salt, 2 parts by weight of the ethylene bisdithiocarbamate, and between about 0.01 and about 0.1 parts by weight of the benzoporphyrin compound.

40 Claims, No Drawings

FUNGICIDAL COMPOSITIONS FOR THE ENHANCEMENT OF TURF QUALITY

RELATED APPLICATIONS

This application is a continuation-in-part of U.S. patent application Ser. No. 08/003,632, filed 12 May 1994 (U.S. Pat. No. 5,336,661).

FIELD OF THE INVENTION

The present invention relates to methods and compositions for the enhancement of turf quality and the control of crown and root rot in turfgrass, and more particularly to synergistic combinations of fungicides useful therefore.

BACKGROUND OF THE INVENTION

Crown and root rot is a serious disease of turfgrasses, especially highly maintained turfgrasses as found in lawns, golf courses, sod farms, and other landscape architecture applications. Current techniques for controlling this disease are not entirely satisfactory, and there is a continuing need for new treatments thereof.

Horriere et al. U.S. Pat. No. 4,698,334 and Horriere et al. U.S. Pat. No. 4,806,445 propose fungicidal compositions based on alkyl phosphites in combination with various contact fungicides such as Mancozeb. These compositions are useful for treating mildew in vines. Ducret et al. U.S. Pat. No. 4,139,616 describes fungicidal compositions based on alkyl phosphites. None of these references relate to the treatment of turfgrasses.

Lucas U.S. Pat. No. 5,336,661 discloses methods of enhancing turf quality of bentgrass using compositions comprising a mixture of a monoester salt of a phosphorous acid, and an ethylenebisdithiocarbamate contact fungicide.

High quality, healthy turfgrass is essential to the golfing industry. Accordingly, there remains a need in the art for fungicidal compositions which enhance turf quality and protect against crown and root rot in turfgrass to provide high quality, healthy turfgrass.

SUMMARY OF THE INVENTION

As a first aspect, the present invention provides a fungicidal composition for enhancing the quality of turfgrass and protecting against crown and root rot. The compositions comprise a synergistic combination of:

(a) a monoester salt of a phosphorous acid of Formula (I):

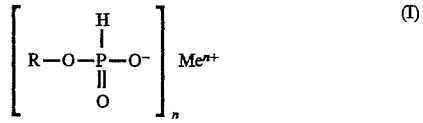

wherein:

R is an alkyl radical having 2 to 4 carbon atoms,

Me is an alkali metal, alkaline earth metal, or aluminum atom, and n is a whole number from 1 to 3 equal to the valence of Me;

(b) an ethylenebisdithiocarbamate contact fungicide selected from the group consisting of manganese ethylenebisdithiocarbamate and manganese-zinc ethylenebisdithiocarbamate; and (c) a benzoporphyrin compound.

As a second aspect, the present invention provides a method of enhancing turf quality and protecting against crown and root rot. The method comprises applying (a) a monoester salt of a phosphorous acid of Formula (I) above, (b) an ethylenebisdithiocarbamate contact fungicide, and (c) a benzoporphyrin compound.

The compounds are applied in an amount effective to enhance turf quality and/or protect against crown and root rot.

The benzoporphyrin compounds useful in the method of the present invention include substituted and unsubstituted-benzoporphyrins and derivatives thereof. Suitable benzoporphyrins include tetrabenzoporphyrins alkyl-substituted methylbenzylporphyrins, halo-substituted benzoporphyrins, and the like. According to one embodiment, the benzoporphyrin is a coordination complex of the Formula $L_1L_2$—$X_1X_2$—$L_3L_4$, wherein $X_1$ and $X_2$ are each H or $X_1$ and $X_2$ together are a transition metal, and $L_1$, $L_2$, $L_3$, and $L_4$ are each independently substituted or unsubstituted isoindole groups, and wherein $L_1$, $L_2$, $L_3$, and $L_4$ are covalently joined to one another. In one preferred coordination complex, $L_1$, $L_2$, $L_3$, and $L_4$ together form a ligand of Formula (II)

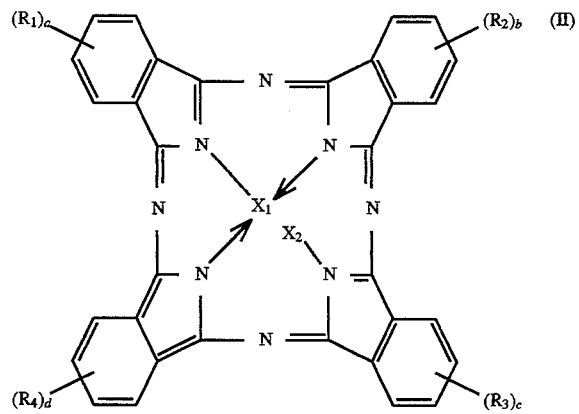

wherein a, b, c, and d are each independently selected from positive integers 0–4, and $R_1$, $R_2$, $R_3$, and $R_4$ are each independently selected from the group consisting of H, halo, $C_{1-20}$ substituted or unsubstituted, saturated or unsaturated, linear, branched or cyclic alkyl, alkoxy, alkylamino, alkylthio, onium, sulphonium, sulphate, and carboxylate.

The foregoing and other aspects of the present invention are explained in detail in the derailed description set forth below.

DETAILED DESCRIPTION OF THE INVENTION

The methods and compositions described herein are useful for improving turf quality and color in turfgrasses. In addition, the methods and compositions described herein are useful for treating crown and root rot in turfgrass. Crown and root rot, which causes a decline in turfgrass quality during hot, wet weather, is a disease complex apparently caused by *Pythium* species and *Rhizoctonia* species in combination with environmental and management stresses.

Monoester salts of phosphorus acids useful for carrying out the present invention, as given in Formula (I) above, are known. See, e.g., Ducret et al. U.S. Pat. No. 4,139,616, Horriere et al. U.S. Pat. No. 4,698,334, and Horriere et al. U.S. Pat. No. 4,806,445, (the disclosures of all U.S. patents cited herein are to be incorporated herein by reference). Examples include calcium ethyl phosphite, sodium ethyl phosphite, aluminum ethyl phosphite, magnesium isopropyl phosphite, calcium isopropyl phosphite, aluminum isopropyl phosphite, magnesium ethyl phosphite, magnesium isobutyl phosphite, magnesium sec-butyl phosphite, calcium isobutyl phosphite, aluminum N-butyl phosphite, aluminum sec-butyl phosphite, and aluminum isobutyl phosphite. Most preferred is aluminum ethyl phosphite (also called aluminum tris (O-ethyl phosphonate)).

Metallic ethylenebisdithiocarbamate contact fungicides, such as maneb (manganese ethylenebisdithiocarbamate) and mancozeb (manganese-zinc ethylene bisdithiocarbamate), are known. See, e.g., Horriere et al. U.S. Pat. No. 4,698,334, and Horriere et al. U.S. Pat. No. 4,806,445. Mancozeb is currently preferred.

Benzoporphyrin compounds are the preferred class of porphine compounds and derivatives thereof, which are useful in the methods of the present invention. Examples of useful porphine compounds include substituted and unsubstituted porphines and derivatives thereof. Suitable derivatives of porphines include substituted and unsubstituted porphyrins. The porphyrins may be benzoporphyrins such as tetrabenzoporphyrins, alkyl-substituted benzylporphyrins, halo-substituted benzoporphyrins, and the like. According to one embodiment, the benzoporphyrin is a coordination complex of the Formula $L_1L_2$—$X_1X_2$—$L_3L_4$, wherein $X_1$ and $X_2$ are each H or $X_1$ and $X_2$ together are a transition metal, and $L_1$, $L_2$, $L_3$, and $L_4$ are each independently substituted or unsubstituted isoindole groups, and wherein $L_1, L_2, L_3$, and $L_4$ are covalently joined to one another (e.g., through a nitrogen or carbon atom, preferably a nitrogen atom). As will be apparent, they are covalently joined as a cyclic structure, i.e., —$L_1$—$L_2$—$L_3$—$L_4$-cy, where cy means $L_4$ is covalently joined to $L_1$. Preferably, $X_1$ and $X_2$ together are a transition metal from Groups IB and VIIIB. The isoindole groups represented by $L_1, L_2, L_3$, and $L_4$ may be unsubstituted, or alternatively, they may be each independently substituted from 1 to 4 times with a substituent selected from the group consisting of halogen, $C_{1-20}$ substituted or unsubstituted, saturated or unsaturated, linear, branched or cyclic alkyl, alkoxy, alkylamino, alkylthio, onium, sulphonium, sulphate, and carboxylate.

In one preferred embodiment of the coordination complex of $L_1L_2$—$X_1X_2$—$L_3L_4$, $L_1$, $L_2$, $L_3$, and $L_4$ together form a ligand of Formula (II)

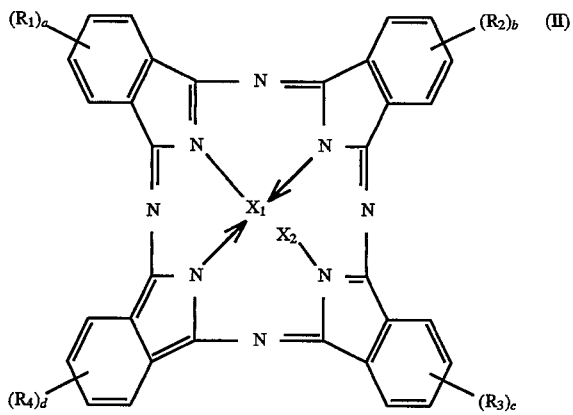

wherein a, b, c, and d are each independently selected from positive integers 0-4, and $R_1$, $R_2$, $R_3$, and $R_4$ are each independently selected from the group consisting of H, halogen, $C_{1-20}$ substituted or unsubstituted, saturated or unsaturated, linear, branched or cyclic alkyl, alkoxy, alkylamino, alkylthio, onium, sulphonium, sulphate, and carboxylate.

Examples of suitable benzoporphyrins of the coordination complex $L_1L_2$—$X_1X_2$—$L_3L_4$ include phthalocyanine dyes. Suitable phthalocyanine dyes may be metal-free phthalocyanines, or metal phthalocyanines. The metal of metal phthalocyanines may be selected from alkali metals, alkali earth metals and transition metals, with transition metals being preferred. Examples of suitable metals include but are not limited to, lithium, sodium, potassium, rubidium and cesium from the alkali metal family; berillium, magnesium, calcium, strontium, barium, and radium from the alkali earth metal family; and copper, silver, gold, zinc, cadmium, mercury, scandium, yittrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium and platinum from the transition metal family. Copper, nickel, cobalt, iron, and zinc phthalocyanine dyes are particularly preferred in the methods of the present invention.

Phthalocyanine dyes which are useful in the methods of the present invention include subsituted and unsubstituted dyes. Suitable substituted phthalocyanine dyes may be metal-free phthalocyanines, or metal phthalocyanines, and may be substituted from 1 to 4 times on each isoindole group independently. Examples of suitable substituents for the isoindole groups of phthalocyanine dyes include but are not limited to, halogens, substituted or unsubstituted, saturated or unsaturated, linear, branched or cyclic alkyl, alkoxy, alkylamino, alkylthio, onium, sulphonium, sulphate, and carboxylate. Suitable phthalocyanine dyes are commercially available and include but are not limited to Pigment Blue 16, Vat Blue 29, Pigment Blue 15, Heliogen Green GG, Ingrain Blue 14, Ingrain Blue 5, Ingrain Blue 1, Pigment Green 37, and Pigment Green 7. In one preferred embodiment, the phthalocyanine dye is Pigment Blue 15. In another preferred embodiment, the phthalocyanine dye is any phthalocyanine dye other than Pigment Blue 15.

Synergistic combinations of the foregoing three active ingredients (the three together being referred to herein as the "active material") are, in general, 1 part by weight of the compound of Formula (I) above in combination with from 1.5 to 2.5 parts by weight of the metallic ethylenebisdithiocarbamate and from 0.01 to 0.1, preferably 0.04 to 0.05 parts by weight of the benzoporphyrin compound. More preferably, the active material includes 1 part by weight of the compound of Formula (I) above in combination with from 1.75 to 2.25 parts by weight of the metallic ethylenebisdithiocarbamate and from 0.01 to 0.1 parts by weight of the benzoporphyrin compound. A particularly preferred combination is 1 part by weight of the compound of Formula (I) above in combination with 2 parts by weight of the metallic ethylenebisdithiocarbamate and from 0.04 to 0.05 parts by weight of Pigment Blue 15.

The synergistic combinations according to the invention may be used with advantage in admixture with one another or with other known fungicides, such as basic salts or hydroxides of copper (oxychloride, oxysulphate), (tetrahydro)phthalimides (Captan, Captafol, Folpel), methyl 1-(butylcarbamoyl)-2-benzimidazolecarbamate (Benomyl), thiophanates such as dimethyl (1,2-phenylene)bis(iminocarbonothioyl)bis(carbamate) (Thiophanate-methyl), tetrachloroisophthalonitrile (Chlorothalonil), 3-(3,5-dichlorophenyl)-N-(1-methylethyl)-2,4-dioxo-1-imidazolidine carboxamide (Iprodione), 1-[2-(2,4-dichlorophenyl)-4-propyl-1,3-dioxolan-2-yl methyl]-1H-1,2,4-triazole (Propiconazole) 1-(4-chlorophenoxy)-3,3-dimethyl-1(1H-1,2,4-triazol-1-yl)-2-butanone (Triadimafon) or other fungicides, either to complete the range of activity of the compounds according to the invention or to increase their persistence.

The synergistic combinations according to the invention may also be mixed with other fungicidal, anti-mildew phosphorus derivatives, especially 2-hydroxy-1,3,2-dioxaphospholanes, β-hydroxy ethyl phosphites and phosphorous acid and its salts.

For their practical application, the active ingredients in the synergistic combinations are used as part of a formulated product which, as a rule, contains a support and/or a surfactant in addition to the active material according to the invention.

In the context of the invention, a support is an organic or mineral, natural or synthetic material with which the active material is associated to facilitate its application to plants, seeds or soil, or its transportation and/or handling. The support can be solid (clays, natural or synthetic silicates, resins, waxes, solid fertilizers) or fluid (water, alcohols, ketones, petroleum fractions, chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain from 20 to 95% by weight of the active material, and they normally contain, in addition to a solid support, from 0 to 5% by weight of a wetting agent, from 3 to 10% by weight of a dispersant and, when necessary, from 0 to 10% by weight of one or more stabilizers and/or other additives, such as penetration agents, adhesives or anti-lumping agents, colorants, etc.

One example of the compositions of a wettable powder is given in Table 1 below:

TABLE 1

| Compound | % by wt. |
| --- | --- |
| active material | 80 |
| calcium lignosulphate (deflocculant) | 5 |
| anionic wetting agent | 1 |
| antilumping silica | 5 |
| kaolin (filler) | 9 |

Powders soluble in water are obtained by mixing from 20 to 95% by weight of the active material, from 0 to 10% of an antilumping agent, the remainder being a hydrosoluble filler mainly a salt.

An example of a composition of the present invention as a soluble powder is given in Table 2 below:

TABLE 2

| Compound | % by wt. |
| --- | --- |
| active material | 70 |
| anionic wetting agent | 0.5 |
| antilumping silica | 5 |
| sodium sulfate (soluble filler) | 24.5 |

Aqueous dispersions and emulsions, for example compositions obtained by diluting with water a wettable powder or an emulsifiable concentrate according to the invention, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or thickeners, thixotropic agents, stabilizers or sequestrants, as well as other active materials known to have pesticidal properties, especially acaricides or insecticides.

The present invention can be practiced with all turfgrasses, including cool season turfgrasses and warm season turfgrasses. Examples of cool season turfgrasses are Bluegrasses (Poa L.), such as Kentucky Bluegrass (*Poa pratensis* L.), Rough Bluegrass (*Poa trivialis* L.), Canada Bluegrass (*Poa compressa* L.), Annual Bluegrass (*Poa annua* L.), Upland Bluegrass (*Poa glaucantha* Gaudin), Wood Bluegrass (*Poa nemoralis* L. ), and Bulbous Bluegrass (*Poa bulbosa* L. ); the Bentgrasses and Redtop (Agrostis L.), such as Creeping Bentgrass (*Agrostis palustris* Huds.), Colonial Bentgrass (*Agrostis tenius* Sibth.), Velvet Bentgrass (*Agrostis canina* L.), South German Mixed Bentgrass (Agrostis L.), and Redtop (*Agrostis alba* L.); the Fescues (Festuca L.), such as Red Fescue (*Festuca rubra* L.), Chewings Fescue (*Festuca rubra* var. commutata Gaud.), Sheep Fescue (*Festuca ovina* L.), Hard Fescue (*Festuca ovina* var. duriuscula L. Koch), Hair Fescue (*Festuca capillata* Lam.), Tall Fescue (*Festuca arundinacea* Schreb.), Meadow Fescue (*Festuca elatior* L.); the Ryegrasses (Lolium L.), such as Perennial Ryegrass (*Lolium perenne* L.), Italian Ryegrass (*Lolium multifiorum* Lam.); the Wheatgrasses (Agropyron Gaertn.), such as Fairway Wheatgrass (*Agropyron cristatum* (L.) Gaertn.), Western Wheatgrass (*Agropyron smithii* Rydb.). Other cool season turfgrasses include Beachgrass (Ammophila Host.), Smooth Brome (*Bromus inermis* Leyss.), Timothy (Phleum L.), Orchardgrass (*Dactylis glomerata* L.), Crested Dog's-Tail (*Cynosurus cristatus* L.). Examples of warm season turfgrasses are the Bermudagrasses (Cynodon L. C. Rich), Zoysiagrasses (Zoysia Willd.), St. Augustinegrass (*Stenotaphrum secundatum* (Walt.) Kuntze), Centipedegrass (*Eremochioa ophiuroides* (Munro.) Hack.), Carpetgrass (Axonopus Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.), Blue Grama (*Bouteloua gracilis* (H.B.K.) Lag. ex Steud.), and Sideoats Grama (*Bouteloua curtipendula* (Michx. Torr.). Cool season turfgrasses are preferred. More preferred is Bluegrass, Bentgrass and Redtop, Fescue, and Ryegrass. Bentgrass is most preferred.

The active materials are, in general, applied to turfgrass either together or separately by spraying a liquid formulation (e.g., an aqueous formulation, including emulsions, or an oil-based formulation) thereof on the turfgrass. The ethylenebisdithiocarbamate contact fungicide is typically applied in an amount of from 10 to 25 pounds per acre (about 10 to 25 Kilograms per Hectare), more preferably in an amount of from 15 to 20 pounds per acre (about 15 to 20 Kg per hectare), and still more preferably in an amount of from 17 to 18 pounds per acre (about 17 to 18 Kg per Hectare). The compound of Formula (I) is, in general, applied in an amount of from ⅖ to ⅔, or more preferably ½, times the amount of the ethhylenebisdithiocarbamate contact fungicide (e.g., from about 5 to 17 pounds per acre).

The following examples are provided to illustrate the present invention, and should not be construed as limiting thereof.

EXAMPLES 1–3

These examples were carried out to identify fungicide and combinations thereof which will improve turf quality and color, and have activity against crown and root rot and brown patch. Fungicides were evaluated on a one-year-old stand of the bentgrass cultivar "Penncross" planted in Raleigh, N.C., USA. The bentgrass was planted in native soil and maintained under conditions similar to a golf green with a mowing height of 0.635 cm (0.25 inches). The fungicides which have activity against *Pythium* species include KOBAN™ (active ingredient: etridiazole) obtained from Grace-Sierra, ALIETTE™ (active ingredient: fosetyl- Al) obtained from Rhone-Poulenc, and SUBDUE™ (active ingredient: metalaxyl) obtained from Ceba-Giegy. The fungicides which have activity against *Pythium* and *Rhizoctonia* species is FORE™ (active ingredient: mancozeb, also including Pigment Blue 15) obtained from Rhom and Haas, MANZATE™ (active ingredient: mancozeb) obtained from DuPont, LESCO MN80™ (active ingredient: mancozeb) obtained from Lesco, PENCOZEB DF 75™ (active ingredient: mancozeb) obtained from Elf Atochem, PROTECT DG 80™ (active ingredient: mancozeb) obtained from W. A. Cleary, and DITHANE™ (active ingredient: mancozeb) obtained from Rhom and Haas.

The fungicides were applied separately and in combination at labelled rates to 1.5 m×1.5 m (5 ft×5 ft) plots of bentgrass prior to evidence of any decline in turf quality due to crown and root rot. A $CO_2$ backpack sprayer was used to apply the fungicide treatments at (30 lbs psi) using TEE-JET™ 8004 nozzles to apply 9.5 liters (2.5 gallons) of fungicide dilutions per 93 square meters (1000 sq ft). The fungicides were initially applied and subsequently reapplied according to a 14 day schedule. In some experiments, an electrical pump sprayer was used to apply the treatments at 30 psi using a Teejet 8004 nozzle.

Turf quality, color and percent disease ratings were recorded weekly, based on a scale from 1–9, with 9 being ideal turf quality and color and 1 being all turf dead. The percent disease ratings were calculated based on the percent of area in each plot showing symptoms of brown patch. Turf quality and color ratings were used as an indicator of the health of the bentgrass and the amount of decline associated with crown and root rot. *Pythium* and *Rhizoctonia* species of fungi were isolated from the bentgrass in the experiment during the test period.

Table 1A below indicates that an improvement in turf quality and color from application of ALIETTE™ +FORE™ (treatment #4), observed with a turf quality of 7.5 and a turf color of 7.8 with 9 being ideal. The combination of ALIETTE™+MANZATE™ had a lower turf quality rating of 6.8 and a turf color of 7.0.

TABLE 1A

ALIETTE ™/FORE ™ Interaction

| Trt. No. | Pesticide Name | Formu. | LBai/A | Turf Quality | Turf Color | % Brown Patch | Disease Control |
|---|---|---|---|---|---|---|---|
| 01 | CHECK | — | — | 4.5 | 5.3 | 50.0 | 0 |
| 02 | ALIETTE ™ | WDG 80 | 8.712 | 6.5 | 6.8 | 0 | 100.0 |
|  | CHP26019 | WDG 50 | 2.72 |  |  |  |  |
| 03 | ALIETTE ™ | WDG 80 | 8.712 | 6.8 | 7.0 | 0 | 100.0 |
|  | MANZATE | WP 70 | 16.34 |  |  |  |  |
| 04 | ALIETTE ™ | WDG 80 | 8.712 | 7.5 | 7.8 | 0 | 100.0 |
|  | FORE ™ | WP 80 | 17.42 |  |  |  |  |
| 05 | ALIETTE ™ | WDG 80 | 8.712 | 5.8 | 5.5 | 0 | 100.0 |
|  | PROSTAR | WP 50 | 5.445 |  |  |  |  |
| 06 | ALIETTE ™ | WDG 80 | 8.712 | 6.3 | 6.8 | 0 | 100.0 |
|  | DACONIL | WDG 90 | 14.7 |  |  |  |  |
| 07 | FORE ™ | WDG 80 | 17.42 | 6.8 | 7.0 | 2.5 | 91.7 |
| 08 | ALIETTE ™ | WDG 80 | 8.712 | 5.0 | 5.8 | 26.3 | 38.0 |
| 09 | ALIETTE ™ | WDG 80 | 4.356 | 6.8 | 7.5 | 0 | 100.0 |
|  | FORE ™ | WP 80 | 8.712 |  |  |  |  |
|  | LSD (0.05) = |  |  | 1.0 | .8 | 9.1 | 23.5 |
|  | STANDARD DEVIATION = |  |  | .7 | .5 | 6.2 | 16.1 |
|  | COEFF. OF VARIABILITY = |  |  | 10.8 | 8.2 | 71.2 | 19.9 |

Table 2 below demonstrates the results of a comparative study of the effects of different formulations of mancozeb. ALIETTE™ and FORE™ was used as a control. The formulations of Daconil, CHP26019, and Banner gave good turf quality and turf color ratings.

TABLE 2

| Trt. No. | Pesticide Name | Formu. | LBai/A | Application Type | Turf Quality | Turf Color | % Brown Patch | Turf Quality | Turf Color | % Brown Patch |
|---|---|---|---|---|---|---|---|---|---|---|
| 01 | CONTROL | Aliette Fore | | | 6.5 | 6.5 | 17.5 | 5.5 | 6.0 | 42.5 |
| 02 | DACOCIL | SG 82.5 | 8.98 | 14 Day | 9.0 | 8.0 | 0 | 8.5 | 8.0 | 0 |
| 03 | CHP 26019 | WG 50 | 2.723 | 14 Day | 8.5 | 7.5 | 0 | 7.0 | 7.0 | 0 |
| 04 | KOBAN | WP 30 | 4.90 | 14 Day | 6.5 | 6.5 | 15.0 | 5.5 | 5.5 | 55.0 |
| 05 | SUBDUE | WP 25 | 1.36 | 14 Day | 6.5 | 6.5 | 12.5 | 5.5 | 6.0 | 47.5 |
| 06 | BAYLETON | WG 25 | 1.36 | 14 Day | 7.0 | 7.5 | 3.8 | 6.5 | 6.5 | 17.5 |
| 07 | BANNER | EC 1.1 | 1.50 | 14 Day | 8.5 | 8.5 | 6.0 | 8.0 | 8.0 | 0 |
| | LSD (0.05) = | | | | 1.6 | 1.6 | 11.1 | 1.4 | .8 | 21.0 |
| | STANDARD DEVIATION = | | | | .6 | .7 | 4.5 | .6 | .3 | 8.6 |
| | COEFF. OF VARIABLITY = | | | | 8.5 | 9.2 | 57.9 | 8.4 | 5.1 | 37.0 |

Table 3 below indicates that similar results were observed in a second test. The data demonstrate that ALIETTE™+FORE™ (treatment #8) gave better turf quality of 7.8 and 8.0 than ALIETTE™+mancozeb+AURAGREEN™ (another type of green dye) (treatment #5) of 7.0 and 7.3. The combination of the experimental formulation of ALIETTE™ and the blue pigment (EXP 10622)+mancozeb (treatment #10) gave higher turf quality ratings of 7.5 and 8.0 than treatment #5, and ratings as high as the ratings for ALIETTE™+FORE™ on most dates.

TABLE 3

ALIETTE ™ /FORE ™ Interaction

| Trt. No. | Pesticide Name | Formu. | LBai/A | Application Type | Phyto rating | Turf Qual. | % Brown Patch | Turf Qual. | Turf Color | % Brown Patch |
|---|---|---|---|---|---|---|---|---|---|---|
| 01 | CONTROL | — | — | — | 1.0 | 5.0 | 25.0 | 5.3 | 6.3 | 15.0 |
| 02 | NCAD 1 | SG 100 | 0.545 | 14 DAY | 1.0 | 4.8 | 2.3 | 5.0 | 7.5 | 16.3 |
| 03 | NCAD 1 ALIETTE ™ | SG 100 WDG 80 | 0.545 8.712 | 14 DAY 14 DAY | 1.8 | 5.8 | 15.0 | 6.3 | 7.5 | 5.0 |
| 04 | NCAD 1 MANCOZEB | SG 100 WDG 80 | 0.545 17.43 | 14 DAY 14 DAY | 1.3 | 6.3 | 7.5 | 6.8 | 7.8 | 0 |
| 05 | NCAD 1 MANCOZEB ALIETTE ™ | SG 100 WDG 80 WDG 80 | 0.545 17.43 8.712 | 14 DAY 14 DAY 14 DAY | 5.5 | 7.0 | 2.5 | 7.3 | 6.8 | 0 |
| 06 | ALIETTE ™ | WDG 80 | 8.712 | 14 DAY | 2.5 | 5.3 | 16.3 | 6.0 | 6.3 | 2.5 |
| 07 | MANCOZEB | WDG 80 | 17.43 | 14 DAY | 2.0 | 6.0 | 13.8 | 6.5 | 6.8 | 8.8 |
| 08 | ALIETTE ™ FORE ™ | WDG 80 WP 80 ™ | 8.712 17.43 | 14 DAY 14 DAY | 1.0 | 7.8 | 0 | 8.0 | 8.0 | 0 |
| 09 | EXP10622 | WDG 80 | 8.712 | 14 DAY | 1.5 | 5.8 | 10.0 | 6.5 | 6.8 | 6.3 |
| 10 | EXP10622 MANCOZEB | WDG 80 WP 80 ™ | 8.712 17.43 | 14 DAY 14 DAY | 3.3 | 7.5 | 0 | 8.0 | 7.5 | 0 |
| | LDS (0.05) = | | | | .8 | 1.0 | 9.4 | .6 | 1.0 | 6.8 |
| | STANDARD DEVIATION = | | | | .6 | .7 | 6.5 | .4 | .7 | 4.7 |
| | COEFF. OF VARIABLITY = | | | | 27.2 | 11.0 | 58.4 | 5.9 | 9.4 | 87.3 |

Table 4 is a comparative study of the effects of different formulations of mancozeb. The formulations of FORE™ WP80™ and FL4.0™, which contain mancozeb+Pigment Blue 15, gave better turf quality and turf color than other formulations of mancozeb without the Pigment Blue 15. Treatment #7 of ALIETTE™+FORE™FL4.0™+ BLENDEX™ (a blending agent) gave better results than treatment #2. Treatment #7 contains more Pigment Blue 15 than treatment #2.

TABLE 4

ALIETTE ™ /MANCOZEB Interactions

| Trt. No. | Pesticide Name | Formu. | LBai/A | Application Type | Turf Quality | Turf Color | % Brown Patch | Turf Quality | Turf Color | % Brown Patch | Turf Quality | Turf Color | % Brown Patch | Turf Quality | Turf Color |
|---|---|---|---|---|---|---|---|---|---|---|---|---|---|---|---|
| 01 | CONTROL | — | — | — | 3.8 | 4.5 | 60.0 | 3.3 | 4.0 | 67.5 | 2.8 | 3.8 | 75.0 | 4.8 | 6.3 |
| 02 | ALIETTE ™ | WDG 80 | 8.712 | 14 DAY | 7.0 | 7.0 | 10.0 | 7.8 | 7.5 | 5.0 | 7.3 | 7.0 | 5.0 | 7.0 | 6.8 |
|  | FORE ™ | WP 80 ™ | 17.42 | 14 DAY |  |  |  |  |  |  |  |  |  |  |  |
| 03 | ALIETTE ™ | WDG 80 | 8.712 | 14 DAY | 6.0 | 6.3 | 12.5 | 6.0 | 6.0 | 1.3 | 6.0 | 6.0 | 8.8 | 5.8 | 5.3 |
|  | LESCO MN | DG 80 | 17.42 | 14 DAY |  |  |  |  |  |  |  |  |  |  |  |
| 04 | ALIETTE ™ | WDG 80 | 8.712 | 14 DAY | 6.3 | 6.5 | 13.8 | 6.0 | 6.0 | 2.5 | 6.0 | 6.3 | 12.5 | 6.0 | 5.5 |
|  | PENICOZEB | DF 75 | 17.42 | 14 DAY |  |  |  |  |  |  |  |  |  |  |  |
| 05 | ALIETTE ™ | WDG 80 | 8.712 | 14 DAY | 6.0 | 6.5 | 11.3 | 6.3 | 6.3 | 5.0 | 6.3 | 6.3 | 8.8 | 5.6 | 5.3 |
|  | PROTECT | DG 80 | 17.42 | 14 DAY |  |  |  |  |  |  |  |  |  |  |  |
| 06 | ALIETTE ™ | WDG 80 | 8.712 | 14 DAY | 6.8 | 7.0 | 6.3 | 6.8 | 6.8 | 7.5 | 7.3 | 7.8 | 3.8 | 7.5 | 7.5 |
|  | FORE ™ | FL 4.0 ™ | 17.42 | 14 DAY |  |  |  |  |  |  |  |  |  |  |  |
| 07 | ALIETTE ™ | WDG 80 | 8.712 | 14 DAY | 7.0 | 7.3 | 5.0 | 8.5 | 7.8 | 0 | 8.0 | 8.0 | 1.3 | 8.0 | 8.0 |
|  | FORE ™ | FL 4.0 ™ | 17.42 | 14 DAY |  |  |  |  |  |  |  |  |  |  |  |
|  | BLENDEX | % C | | 14 DAY |  |  |  |  |  |  |  |  |  |  |  |
| 08 | ALIETTE ™ | WDG 80 | 8.712 | 14 DAY | 4.3 | 4.8 | 46.3 | 5.8 | 6.0 | 2.5 | 5.8 | 5.8 | 17.5 | 6.0 | 5.5 |
|  | DITHANE | WDG 75 | 17.42 | 14 DAY |  |  |  |  |  |  |  |  |  |  |  |
| 09 | LESCO MN | DG 80 | 17.42 | 14 DAY | 4.8 | 5.5 | 21.3 | 5.0 | 5.3 | 8.8 | 4.8 | 4.8 | 22.5 | 5.8 | 6.0 |
|  | LDS (0.05) = |  |  |  | 1.0 | .7 | 21.3 | .5 | .7 | 10.6 | .7 | .6 | 9.1 | .7 | 1.1 |
|  | STANDARD DEVIATION = |  |  |  | .7 | .5 | 14.6 | .4 | .5 | 7.0 | .5 | .4 | 6.2 | .5 | .7 |
|  | COEFF. OF VARIABLITY = |  |  |  | 11.7 | 8.3 | 70.6 | 5.9 | 7.4 | 63.3 | 8.5 | 6.6 | 36.1 | 7.6 | 11.6 |

Overall, the results indicate that the combination of ALIETTE™+FORE™, containing the Pigment Blue 15, provides a better improvement in turf quality and color over other combinations of ALIETTE™ and mancozeb without the Pigment Blue 15. The results demonstrate that the presence of the Pigment Blue 15, enhances the activity of the ALIETTE™ and mancozeb in a synergistic interaction.

The foregoing is illustrative of the present invention and is not to be construed as limiting thereof. The invention is defined by the following claims, with equivalents of the claims to be included therein.

That which is claimed is:

1. A method of enhancing turf quality in turfgrass which comprises applying to said turfgrass in an amount effective to enhance turf quality:

(a) 1 part by weight of a monoester salt of a phosphorous acid of Formula (I):

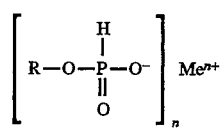

wherein:

R is an alkyl radical having 2 to 4 carbon atoms,

Me is an alkali metal, alkaline earth metal, or aluminum atom, and n is a whole number from 1 to 3 equal to the valence of Me;

(b) from 1.5 to 2.5 parts by weight of an ethylenebisdithio-carbamate contact fungicide selected from the group consisting of manganese ethylenebis-dithiocarbamate and manganese-zinc ethylenebis-dithiocarbamate; and (c) from 0.01 to 0.1 parts by weight of a benzoporphyrin compound.

2. The method according to claim 1, wherein said benzoporphyrin compound is a tetrabenzoporphyrin compound.

3. The method according to claim 1, wherein said benzoporphyrin compound is a coordination complex of the Formula $L_1L_2$—$XX_2$—$L_3L_4$, wherein $X_1$ and $X_2$ are each H or $X_1$ and $X_2$ together are a transition metal, and $L_1$, $L_2$, $L_3$, and $L_4$ are each substituted or unsubstituted isoindole groups; and wherein $L_1$, $L_2$, $L_3$, and $L_4$ are covalently joined to one another.

4. The method according to claim 1, wherein said benzoporphyrin compound is a coordination complex of the Formula $L_1L_2$—$X_1X_2$—$L_3L_4$, wherein $X_1$ and $X_2$ are each H or $X_1$ and $X_2$ together are a transition metal; and $L_1$, $L_2$, $L_3$, and $L_4$ together form a ligand of Formula (II)

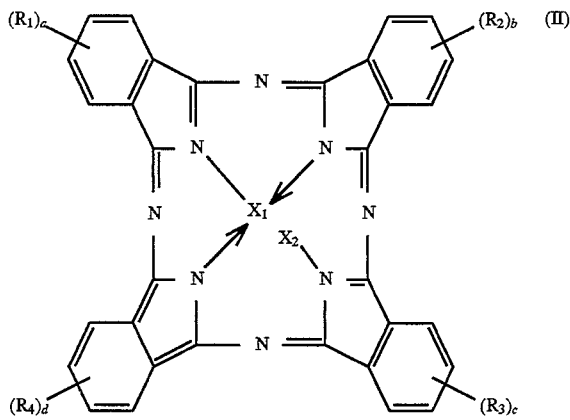

wherein a, b, c, and d are each independently selected from positive integers 0–4, and $R_1$, $R_2$, $R_3$, and $R_4$ are each independently selected from the group consisting of H, halo, $C_{1-20}$ substituted or unsubstituted, saturated or unsaturated, linear, branched or cyclic alkyl, alkoxy, alkylamino, alkylthio, onium, sulphonium, sulphate, and carboxylate.

5. A method according to claim 1, wherein said benzoporphyrin compound is a phthalocyanine compound.

6. The method according to claim 1, wherein said step of applying comprises applying 1 part by weight of said monoester salt of a phosphorous acid, 2 parts by weight of said ethylenebisdithiocarbamate contact fungicide, and 0.05 parts by weight of said benzoporphyrin compound.

7. The method according to claim 5, wherein said phthalocyanine compound is Pigment Blue 15.

8. The method according to claim 5, wherein said phthalocyanine compound is not Pigment Blue 15.

9. The method according to claim 1, wherein said step of applying is carried out by applying said monoester salt, said contact fungicide, and said benzoporphyrin compound to said turfgrass together in a common carrier.

10. The method according to claim 1, wherein said turfgrass is bentgrass.

11. The method according to claim 1, wherein said turfgrass is bermudagrass.

12. The method according to claim 1, wherein said ethylenebisdithiocarbamate is applied to said turfgrass in an amount of from 10 to 25 pounds per acre.

13. A fungicidal composition for enhancing turf quality in turfgrass comprising:

(a) 1 part by weight of a monoester salt of a phosphorous acid of Formula (I):

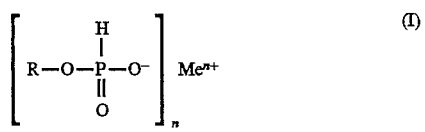

wherein:

R is an alkyl radical having 2 to 4 carbon atoms,

Me is an alkali metal, alkaline earth, or aluminum atom, and n is a whole number from 1 to 3 equal to the valence of Me;

(b) from 1.5 to 2.5 parts by weight of an ethylenebisdithiocarbamate contact fungicide selected from the group consisting of manganese ethylenebisdithiocarbamate and manganese-zinc ethylenebisdithiocarbamate; and (c) from 0.01 to 0.1 parts by weight of a benzoporphyrin compound.

14. The composition according to claim 13, wherein said benzoporphyrin compound is a tetrabenzoporphyrin compound.

15. The composition according to claim 13, wherein said benzoporphyrin compound is a coordination complex of the Formula $L_1L_2$—$X_1X_2$—$L_3L_4$, wherein $X_1$ and $X_2$ are each H or $X_1$ and $X_2$ together are a transition metal, and $L_1$, $L_2$, $L_3$, and $L_4$ are each substituted or unsubstituted isoindole groups; and wherein $L_1$, $L_2$, $L_3$, and $L_4$ are covalently joined to one another.

16. The composition according to claim 13, wherein said benzoporphyrin compound is a coordination complex of the Formula $L_1L_2$—$X_1X_2$—$L_3L_4$, wherein $X_1$ and $X_2$ are each H or $X_1$ and $X_2$ together are a transition metal; and $L_1$, $L_2$, $L_3$, and $L_4$ together form a ligand of Formula (II)

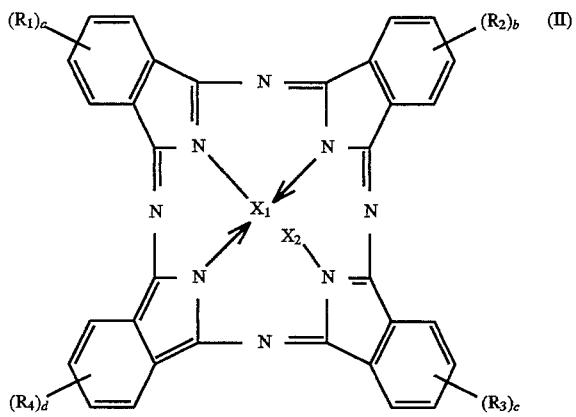

wherein a, b, c, and d are each independently selected from positive integers 0–4, and $R_1$, $R_2$, $R_3$, and $R_4$ are each independently selected from the group consisting of H, halo, $C_{1-20}$ substituted or unsubstituted, saturated or unsaturated, linear, branched or cyclic alkyl, alkoxy, alkylamino, alkylthio, onium, sulphonium, sulphate, and carboxylate.

17. A composition according to claim 13, wherein said benzoporphyrin compound is a phthalocyanine compound.

18. The composition according to claim 13, wherein said ethylenebisdithiocarbamate contact fungicide is manganese-zinc ethylenebisdithiocarbamate.

19. The composition according to claim 13, wherein R is selected from the group consisting of ethyl, propyl, and butyl.

20. The composition according to claim 13, wherein Me is selected from the group consisting of aluminum, calcium, magnesium, and sodium.

21. The composition according to claim 16, wherein a, b, c, and d are 0, and $X_1$ and $X_2$ are H.

22. The composition according to claim 15, wherein $X_1$ and $X_2$ together represent a transition metal selected from the group consisting of Group IB and Group VIIIB transition metals.

23. The composition according to claim 15, wherein $X_1$ and $X_2$ together represent a transition metal selected from the group consisting of cobalt, copper, nickel, iron and zinc.

24. The composition according to claim 15, wherein $X_1$ and $X_2$ together represent copper.

25. The composition according to claim 16, wherein a, b, c, and d are each 2 and $R_1$, $R_2$, $R_3$, and $R_4$ are each halogen.

26. The composition according to claim 16, wherein a, b, c, and d are each 4, and $R_1$, $R_2$, $R_3$, and $R_4$ are each halogen.

27. The composition according to claim 16, wherein a, b, c, and d are each 0, and $X_1$ and $X_2$ together represent copper.

28. The composition according to claim 16, wherein $R_1$, $R_2$, $R_3$, and $R_4$ are each onium.

29. The composition according to claim 16, wherein $R_1$, $R_2$, $R_3$, and $R_4$ are each sulphate.

30. The composition according to claim 13, wherein said compound of Formula (I) is selected from the group consisting of calcium ethyl phosphite, sodium ethyl phosphite, aluminum ethyl phosphite, magnesium isopropyl phosphite, calcium isopropyl phosphite, aluminum isopropyl phosphite, magnesium ethyl phosphite, magnesium isobutyl phosphite, magnesium sec-butyl phosphite, calcium isobutyl phosphite, aluminum N-butyl phosphite, aluminum sec-butyl phosphite, and aluminum isobutyl phosphite.

31. The composition according to claim 13, wherein said compound of Formula (I) is aluminum ethyl phosphite.

32. The composition according to claim 17, wherein said phthalocyanine compound is selected from the group consisting of Pigment Blue 16, Vat Blue 29, Pigment Blue 15, Heliogen Green GG, Ingrain Blue 14, Ingrain Blue 5, Ingrain Blue 1, Pigment Green 37, and Pigment Green 7.

33. The composition according to claim 17, wherein said phthalocyanine compound is Pigment Blue 15.

34. The composition according to claim 17, wherein said phthalocyanine compound is not Pigment Blue 15.

35. The composition according to claim 13, comprising one part by weight of said monoester salt of a phosphorous acid, two parts by weight of said ethylenebisdithiocarbamate contact fungicide, and about 0.05 parts by weight of said benzoporphyrin.

36. The composition according to claim 13, wherein said composition is an aqueous suspension.

37. The composition according to claim 13, wherein said composition is a wettable powder.

38. A fungicidal composition for enhancing the quality of turfgrass, which comprises as the active material a mixture of:

(a) 1 part by weight of aluminum ethyl phosphite;

(b) 2 parts by weight of manganese-zinc ethylenebisdithiocarbamate; and (c) 0.05 parts by weight of Pigment Blue 15.

39. The composition according to claim 38, wherein said composition is an aqueous suspension.

40. The composition according to claim 38, wherein said composition is a wettable powder.

* * * * *

UNITED STATES PATENT AND TRADEMARK OFFICE
CERTIFICATE OF CORRECTION

PATENT NO. : 5,643,852
DATED : July 1, 1997
INVENTOR(S) : Lucas, et. al.

It is certified that error appears in the above-indentified patent and that said Letters Patent is hereby corrected as shown below:

Claim 3, Col. 12, line 55, replace "$XX_2$" with --$X_1X_2$--.

Signed and Sealed this

Twenty-first Day of October 1997

Attest:

BRUCE LEHMAN

Attesting Officer

Commissioner of Patents and Trademarks